United States Patent [19]

Roley

[11] Patent Number: 5,176,823
[45] Date of Patent: Jan. 5, 1993

[54] ODOR CONTROL SYSTEM FOR WASTEWATER SETTLING TANK WITH GAS VELOCITY TEST PROBES

[75] Inventor: John J. Roley, Warrington, Pa.

[73] Assignee: Warminster Fiberglass Company, Southampton, Pa.

[21] Appl. No.: 687,060

[22] Filed: Apr. 18, 1991

[51] Int. Cl.⁵ .............................................. B01D 21/30
[52] U.S. Cl. .................................... 210/85; 73/866.5; 210/87; 210/188; 210/218; 210/539; 210/916; 55/270
[58] Field of Search ................. 210/188, 539, 916, 85, 210/87, 120, 218; 55/270; 73/23.2, 866.5

[56] References Cited

U.S. PATENT DOCUMENTS

| | | | |
|---|---|---|---|
| 4,391,704 | 7/1983 | Anderson | 210/188 |
| 4,767,536 | 8/1988 | Roley | 210/188 |
| 4,883,602 | 11/1989 | Anderson | 210/188 |

OTHER PUBLICATIONS

Publication—"Elimination of Odor at Six Major Wastewater Treatment Plants"—G. David Waltrip & Edwin G. Snyder, Oct. 1985 issue of Journal WPCF—, vol. 57, No. 10, pp. 1027-1032.

*Primary Examiner*—Robert A. Dawson
*Assistant Examiner*—Joseph Drodge
*Attorney, Agent, or Firm*—Michael Ebert

[57] ABSTRACT

An odor control system for a settling tank containing a pool of wastewater to be clarified in which suspended particles are removed by gravitational settling and the water at the surface of the pool is clarified. Supported within the tank is an elongated effluent trough having a weir at one side thereof which extends upwardly therefrom to permit clarified water from the pool to spill over into the trough. Mounted over the trough along its full length is a hood having a side wall which extends into the pool at a position displaced from the weir the hood being constituted by a series of sections. The hood acts to capture noxious gases emitted into a region above the surface of the water therebelow as the clarified water spills over into the trough. The hood is provided with an inlet and an outlet duct whereby atmospheric air drawn through the inlet duct into the region under the hood entrains the emitted gases to produce a gas-laden air stream that flows at a specified velocity and is discharged from the outlet duct into an external scrubber. Formed in each hood section is a closable port providing access for test probes to determine the velocity of the gas-laden stream in the region and the concentration of the gases therein.

8 Claims, 2 Drawing Sheets

ODOR CONTROL SYSTEM FOR WASTEWATER SETTLING TANK WITH GAS VELOCITY TEST PROBES

BACKGROUND OF INVENTION

1. Field of the Invention

This invention relates generally to an odor control system for wastewater settling tanks to capture and treat noxious and ordoriferous gases emitted therefrom, and more particularly to a system that includes a multi-section hood, each section of which is provided with an access port in which test probes are insertable to determine the velocity of the gas-laden air flowing under the hood and the concentration of the gases therein.

2. Status of Prior Art

Sedimentation is the process by which suspended particles heavier than water are removed by gravitational settling. Sedimentation which comes into play in the natural purification of streams and lakes is also widely used in the treatment of sewage and industrial wastes.

Systems for treating sewage and industrial wastes typically include preliminary settling tanks that collect a good part of the suspended of impurities before the clarified effluent is discharged into receiving waters or is subjected to further treatment in secondary settling tanks. In the secondary or final settling tanks, the clarified effluent from the primary tanks are further treated by additional settling and clarification to purify the effluent.

A settling tank has four functional zones; namely, an inlet zone, a settling zone, a sludge zone and an outlet zone. For high efficiency, inlets must distribute the incoming wastewater as uniformly as possible within the tank. In the sludge zone, sludge is worked into a sump from which it is withdrawn by gravity or by a pumping action. The main concern of the present invention is with the outlet zone in which the control of outflow is usually effected by a weir attached to one or both sides of an outlet trough of launder which acts as a lateral spillway.

The Anderson U.S. Pat. No. 4,391,704, discloses an outlet zone whose structure and operation is such as to prevent odoriferous and noxious fumes from entering the atmosphere. Because incoming waste is saturated with noxious gases and easily volatilized compounds, some degree of odor control is generally necessary in a liquid waste treatment system. In sewage, the objectionable compound which predominates is hydrogen sulfide, a colorless gas having an offensive odor. This gas is highly toxic and a strong irritant to eyes and mucous membranes. Hydrogen sulfide is almost always present in sewage, for it is the product of anaerobic decomposition by bacterial present in the sewage and in the sewage treatment system.

With settling tanks and sewage collection systems having significant detention times, the generation of hydrogen sulfide, particularly in warm weather, can be so vigorous that the gases released form the tank create serious problems. Apart form its unpleasant ordor, the presence of hydrogen sulfide in the atmosphere is hazardous to personnel in the vicinity of the tank and may cause permanent injury and even death. And since hydrogen sulfide will combine with moisture in the atmosphere and water on concrete or metal surfaces to form sulfuric acid, this acid may severely corrode the structures.

One known approach to odor control is to fully cover the settling tank. But this approach leaves much to be desired; for when the tank is covered with a concrete or other structure, the reaction of the gases with the structure then gives rise to serious corrosion problems. Moreover, the cost of such a cover is very high.

The outlet zone disclosed in the Anderson patent functions to localize the odoriferous and noxious fumes to the region of the collection trough or launder from which they are extracted, the settling zone of the tank being uncovered. The Anderson invention is based on the recognition that almost all of the noxious gases generated in a settling tank are released as the clarified water spills over the weirs mounted on the sides of the trough; hence by capturing these hazardous gases in the trough region and transporting the captured gases to a gas-control system or in otherwise disposing of the gases, one is able to reduce the discharge of gases into the atmosphere to an acceptably safe level.

The Anderson patent provides an outlet zone for a settling tank in which the trough is covered by a hood that also functions as a scum baffle. In a conventional outlet zone, a baffle which protrudes into the tank water is mounted adjacent to the weir of the trough to prevent grease and other floating matter from being discharged into the trough with the effluent. With the Anderson arrangement, the hood which acts to confine the gases released in the trough has a scum baffle integral therewith.

Inasmuch as the hood in Anderson which covers the trough is required to collect a relatively small volume of air as compared to a cover placed over the entire tank, a significant advantage of this arrangement is that it is not only more effective than a massive tank cover, but is also substantially less expensive to construct, operate and maintain.

Also of prior art interest is the Roley U.S. Pat. No. 4,767,536, which discloses an outlet for extracting noxious gases generated in a settling tank containing a pool of wastewater, the outlet including an effluent trough supported at a raised position in the pool against the tank wall. The trough is provided with a side wall parallel to the tank wall and lying somewhat below the surface of the pool. A weir, supported on this side wall and extending upwardly therefrom, permits clarified water from the surface region of the pool to spill over into the trough.

Overlying the trough and the weir is an odor control hood that includes a horizontal flat walk plate that extends from the tank to the upper edge of a vertical sidewall which extends downwardly into the pool. The sidewall together with the walk plate acts to confine noxious gases emitted into the region above the trough and the weir to prevent their discharge into the atmosphere. The walk plate includes a hatch cover section providing access to the weir when it becomes necessary to scrub and clean the weir.

In an existing settling tank odor control system of the type disclosed in the Roley patent, an external exhauster functions to draw an air stream having noxious gases entrained therein from the region underlying the hood and to feed this stream at a specified velocity to a scrubber. In this installation, the parameters are such as to change all of the gas-laden air beneath the hood several times per hour. The scrubber is designed to take this change rate into account and neutralize hydrogen sulfide ($H_2S$) and other highly odorous sewage gases such as indoles, skatoles, mercaptans and amines before the treated air is discharged into the atmosphere.

However, the rate at which noxious gases are generated and the volume of such gases captured by the hood depends on the nature of the wastewater being treated. Hence a given flow velocity setting may be inadequate in those situations where the concentration of noxious gases in the air stream becomes very high because of the changing character of the wastewater. Also, even if the nature of the wastewater does not change, the amount of noxious gases emitted therefrom varies with the seasons of the year. Thus in hot weather more gases are generated than in cool weather.

As noted previously, the presence of $H_2S$ in the region beneath the hood can have a corrosive effect on the concrete walls defining the trough as well as on metal parts exposed to the gas, for $H_2S$ combines with moisture in the air and with water on the concrete and metal surfaces to produce sulfuric acid. If, therefore, there are stagnant pockets of $H_2S$ in the region under the hood or the flow velocity is too low to withdraw the gas from the hood confined region, over a period of time the resultant acid corrosion may be so damaging as to require major repairs or replacements.

It is essential, therefore, in order to calibrate an odor control system for a wastewater settling tank and maintain it in good working order, that the operator of the system be able periodically to check the gas-laden air stream velocity at a series of designated check points along the region under the hood covering the trough. From this measurement, the operator can determine whether the system is functioning properly under the prevailing conditions or whether correction is required because of some obstruction or impedance at some point in the gas-laden air stream path under the hood. It is also essential, in order to determine whether the system is functioning properly, to measure the concentration of gases at these points to be sure that there is no excessive rise in concentration.

In this way, adjustments can be made by the operator to maintain the odor control system in proper working order and thereby minimize the release of odoriferous gases into the atmosphere as well as to avoid corrosion. However, with an odor control hood arrangement of the types disclosed in the Anderson and Roley patents, the operator has no access to the trough region confined by the hood structure, and it is not possible to test the velocity of the gas-laden air stream flowing through the region or the concentration of gases therein.

Thus while the hood in the Roley patent is provided with hatch covers along the length of the trough, thereby giving access to the weir for cleaning purposes, when a hatch cover is raised the system is short-circuited and the airtight seal broken, thereby causing intereference with the specified air flow requirements.

One reason why it is important to know the prevailing gas concentration in the region under the hood is that in order to fully neutralize these gases, the scrubber into which the gases are fed must include chemicals for this purpose in an amount and strength sufficient for a predetermined volume and concentration of incoming gas. Hence in a given situation, a measurement of gas concentration may tell the operator of the system that the chemical charge in the scrubber is insufficient under prevailing conditions and must be increased.

SUMMARY OF INVENTION

In view of the foregoing, the main object of this invention is to provide an odor control system for a wastewater settling tank having means which make it possible while the system is operating to test the velocity of the gas-laden stream flowing through the region underlying the hood covering the effluent trough as well as the concentration of the gases entrained in the stream so as to determine whether the system is working properly or in need of adjustment.

A significant advantage of the invention is that the testing procedure at no time interrupts the operation of the system and can be carried out without difficulty.

More particularly, an object of this invention is to provide in an odor control system of the above type a hood which extends along the full length of the effluent trough supported in the settling tank and covers this trough to capture the noxious gases which are generated as the clarified wastewater spills over the weir attached to one side wall of the trough, the hood having a series of closable ports at spaced points therealong which afford access to the region enclosed by the hood for test probes for measuring flow velocity and gas concentration.

Still another object of this invention is to provide access ports in an odor control hood, which ports are closable by caps that when in place lie flush with the outer surface of the hood which functions as a walkway.

Yet another object of the invention is to provide access ports for test probes which are so placed on the hood covering the effluent trough as to make it possible to sense prevailing flow velocity and gas concentration conditions without interference from air swirls or water turbulence, whereby accurate readings are obtainable.

Briefly stated, these objects are attained in an odor control system for a settling tank containing a pool of wastewater to be clarified in which suspended particles are removed by gravitational settling and the water at the surface of the pool is clarified. Supported within the tank is an elongated effluent trough having a weir at one side thereof which extends upwardly therefrom to permit clarified water from the pool to spill over into the trough. Mounted over the trough along its full length is a hood having a side wall which extends into the pool at a position spaced from the weir, the hood being constituted by a series of sections, the hood acts to capture noxious gases emitted into a region above the surface of the water as the clarified water spills over into the trough.

The hood is provided with an inlet and an outlet duct whereby atmospheric air drawn through the inlet duct into the region under the hood entrains the emitted gases to produce a gas-laden air stream that flows at a specified velocity through the region and is discharged from the outlet duct into an external scrubber. Formed in each section of the hood is a closable port providing access for test probes to determine the velocity of the gas-laden stream in the region and the concentration of the gases therein.

BRIEF DESCRIPTION OF DRAWINGS

For a better understanding of the invention as well as other objects and further features thereof, reference is made to the following detailed description in which.

DESCRIPTION OF INVENTION

Figure 1:
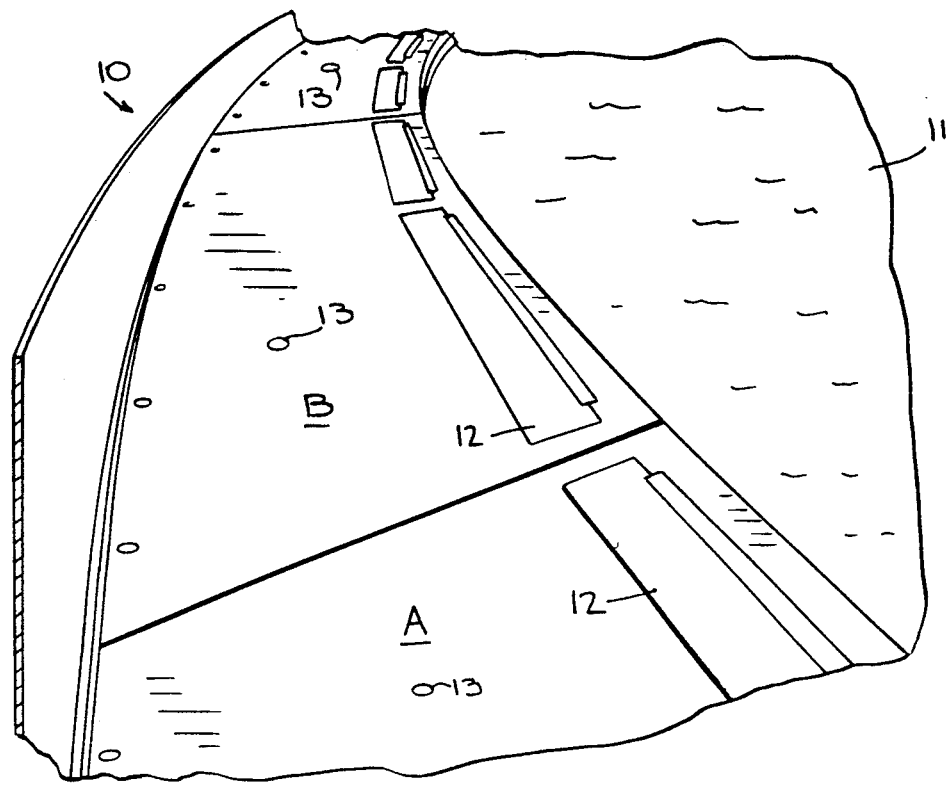
FIG. 1 is a perspective view of a portion of a round wastewater settling tank having an odor control hood, each section of which is provided with a test probe access port in accordance with the invention.

Referring now to FIG. 1, there is shown a portion of a round settling tank 10 is shown containing a pool 11 of wastewater to be clarified. Covering an effluent trough in the tank into which is spilled clarified water from the pool, is an odor control hood in accordance with the invention. The hood is composed of a series of sections, A, B, C, etc., in a ring formation, each section having a hatch cover 12 to provide access to the weir of the trough below the hood. Each section is also provided with a test probe port having a removable cap 13.

Figure 2:
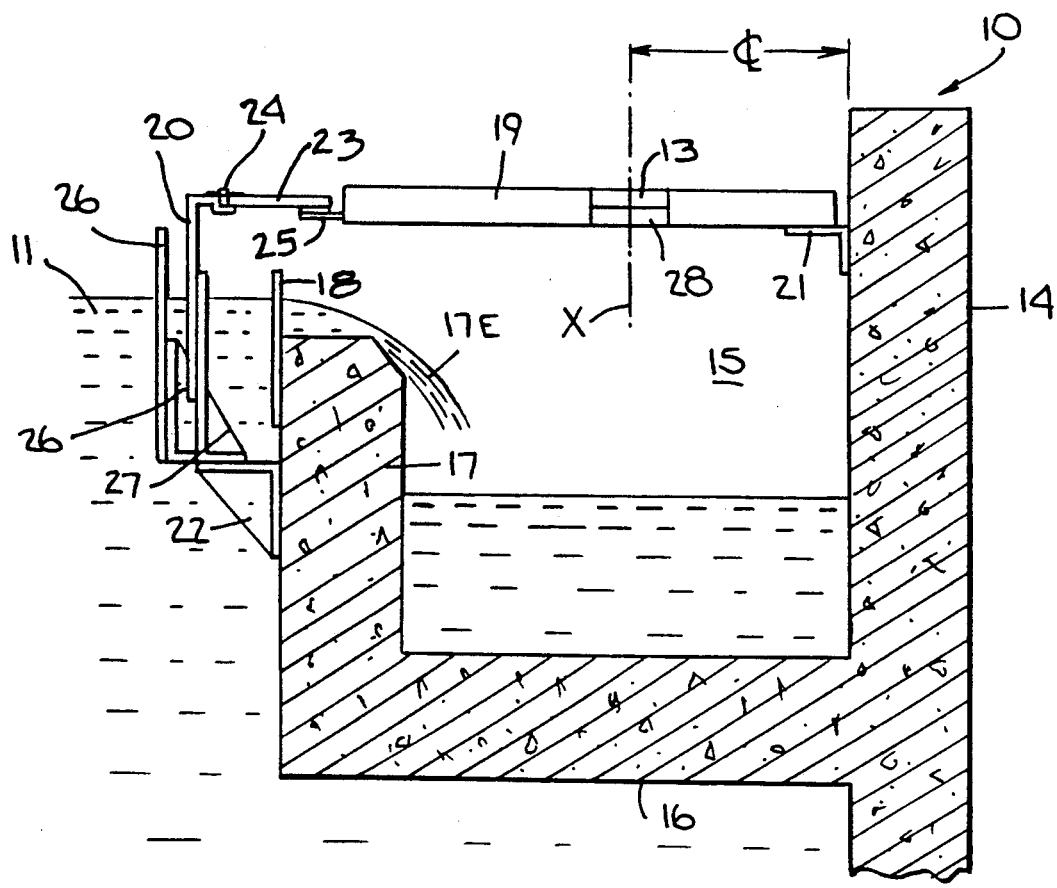
FIG. 2 illustrates, in section, the effluent trough of the settling tank covered by an odor control hood having an access port in accordance with the invention closed by a removable cap.

As shown in FIG. 2, the wastewater settling tank 10, which contains wastewater pool 11, has an outer wall 14 formed of concrete or other suitable structural material capable of holding a large pool of water. While in FIG. 1, tank 10 is shown as round in form, in practice it may be rectangular, in which case the outer wall of the tank is straight.

Supported at an elevated position within the pool against the interior surface of outer tank wall 14 is an effluent trough 15. In practice, the trough can also be formed of concrete so cast as to be integrated with wall 14. Trough 15 is defined by a bottom wall 16 and a side wall 17 parallel to outer wall 14. The height of side wall 17 is such that this wall is below the surface of wastewater pool 11, the surface water being clarified by reason of gravitational settling.

Figure 3:
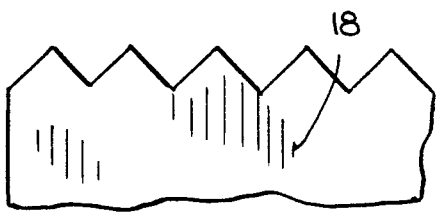
FIG. 3 illustrates, in elevation, the weir attached to the trough.

Supported against side wall 17 and extending upwardly therefrom is a weir 18 which has a sawtooth upper edge. As shown separately in FIG. 3, the sawtooth upper edge extends just above the pool surface to permit clarified water from the pool surface to spill over into effluent trough 11. The upper edge 17E of side wall 17 is chamfered to cause inflowing clarified water to spill downwardly into the trough.

Because the noxious gases emanate largely from the effluent trough, no need exists to cover the entire tank in order to capture these gases, for by covering only the trough and the weir inlet thereto, one can then capture substantially all of the gases. To this end, there is provided a hood including a flat walk plate 19 which overlies effluent trough 15 and weir 18. Walk plate 19 extends horizontally from the inner surface of tank wall 14 to a right-angle flange at the upper edge of a vertical baffle plate 20 extending downwardly into pool 11. Walk plate 19 and baffle plate 20 together act to so confine the atmospheric region above the trough and the weir as to capture the gases emitted from the effluent. Walk plate 19 is secured to tank wall 14 by an angle 21 which when this wall is circular is curved to conform thereto.

Baffle plate 20 which is placed in advance of weir 18 is supported by an outboard bracket 22 mounted on the outer surface of side wall 17. Walk plate 19 includes a hatch cover section 23 hinged to the flange of baffle plate 20 by a stainless steel piano hinge 24. The hatch cover is provided with a recessed cup latch 25.

In practice, scum may be prevented from entering the trough by means of a scum baffle 26 placed in advance of baffle plate 20 and supported by a bracket 27 mounted on top of bracket 22. However, baffle plate 20 also acts as a scum baffle.

Figure 4:
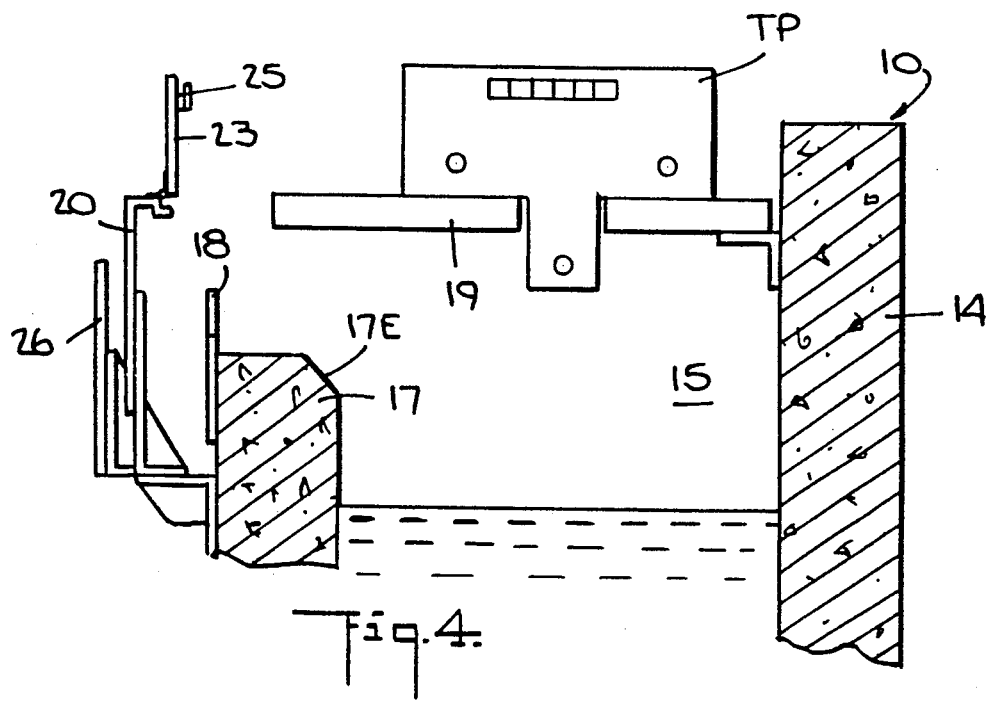
FIG. 4 is the same as FIG. 2, but with the cap removed and a test probe inserted in the access port.

Hatch cover section 23 which is coplanar with walk plate 19 is normally a part of the walkway. This walkway is preferably provided with a non-skid tread. Hence an operator who wishes to inspect the system can walk safely thereover. But should it become necessary to obtain access to weir 18 to scrub and clean the weir, one has merely to swing up the hinged hatch cover 23 to do so, as shown in FIG. 4.

The interior region overlying the surface of the clarified water in trough 15 and the inlet thereto which includes weir 18 is enclosed by the hood defined by the walk plate and the baffle plate to capture the emitted noxious gases. These can be exhausted from this region by a suction pump coupled to a gas control system in the manner described in the Anderson patent, but preferably the gases are exhausted from this region in the manner shown in FIG. 5, to be later described.

In order to make it possible for a test probe to obtain access to the region under the hood through which courses a stream of gas-laden air, walk plate 19 of the hood is provided with a port 28. This port lies in registration with the vertical center line X of trough 15. This line is midway between the interior surface of the inboard and outboard walls 17 and 14 of the trough.

The reason it is important that access port 28 be aligned with the center line of the trough is that the gas-laden air stream flowing directly below the port is substantially free of the turbulence encountered at the inboard side of the trough as a result of water splashing over weir 18 and it also is isolated from the swirling air near the outboard side. The noxious gases emitted from the surface of the water in the trough build up above the waterline in the intermediate zone between the inboard and outboard sides of the trough.

Port 28 is closable by means of the removable cap 13 which in practice may be frictionally-fitted into the port or threadably received therein. When cap 13 is in place to seal the port, it then lies flush with the surface of the walk plate and therefore creates no protuberance that would cause an operator walking along the walk plate to trip or stumble.

Insertable in port 28, as shown in FIG. 4, is the probe of a test instrument TP. While in this figure hatch cover 23 is shown in its raised position to provide access to the weir, when this test instrument is in use, the hatch cover then must be closed to confine the gas-laden air stream to the region under the hood.

Instrument TP, when functioning to measure flow velocity, can be any commercially available instrument for this purpose whose sensor or probe is insertable in the port. And the instrument, when functioning to measure the concentration of $H_2S$, methane, or any other sewage gas, is any commercially available instrument giving a reading of gas concentration in parts per million (PPM). In practice, the odor control system may be said to be in satisfactory working order when the PPM is no higher than 4 or 5. While in FIG. 4, the inserted test probe is shown well above the water line in the trough, in practice the length of the probe should be such as to reach down to a point close to the water line.

The gas-laden air stream velocity and gas concentration readings assist the operator of the system in setting and calibrating the chemical neutralization system for exact levels of gas entrained in the air stream fed into the system.

And because there is an access port at spaced points along the hood structure, one for each hood section, the operator can take readings at each point and thereby locate obstructions in the flow path or other defects in the odor control system. The ease of access to the flow region below the hood to run tests allows the operator at different seasons of the year to recalibrate the gas treatment system or scrubber and thereby effect economies in chemicals, for less gas is generated in cool or cold weather than in warm or hot weather.

With a system in accordance with the invention, accurate data can be collected to evaluate air stream velocity requirements to provide an exact number of air changes per hour and to determine the proper chemical charge to effect complete neutralization of the noxious gases.

THE ODOR CONTROL SYSTEM

Figure 5:
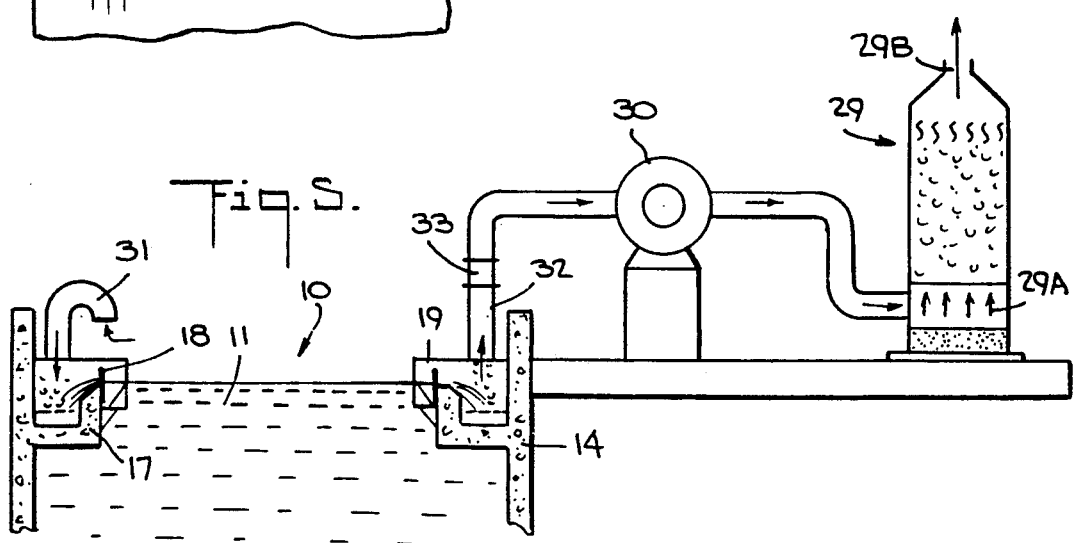
FIG. 5 schematically shows an odor control system in accordance with the invention.

As shown in FIG. 5, the complete odor control system for extracting and neutralizing noxious and odoriferous gases from the wastewater settling tank 10 includes not only the hood structure enclosing effluent trough 15, but also a scrubber 29 and an exhauster 30.

In this complete system, the odor control hood covers the trough 15 and extends the full length thereof. Hence in the case of a round settling tank 10, the hood is annular in form, while with a rectangular tank, the trough and hood are in a straight line. The hood is provided with an inlet duct 31 which supplies atmospheric air into the region above the surface of the clarified water in the trough that is enclosed by the hood. And the hood is also provided with an outlet duct 32 which is coupled to exhauster 30, the blower functioning to draw air at a specified velocity through the region which entrains the noxious gases emitted from the clarified water and to feed the resultant stream of gas-laden air into scrubber 29. Interposed in exhaust duct 32 is an air balancing and calibrating damper 33. The access ports included in the system are not shown in FIG. 5.

In practice, the hood structure and the duct work are preferably fabricated of fiberglass reinforced plastic material, such as polyester resin. The scrubber includes packing material, moisture eliminators, nozzles and headers, a recirculation pump and a neutralizing chemical control system. In operation, atmospheric air drawn into the hood-enclosed region through inlet duct 31 flows at high velocity through the region. The gases emitted from the surface of the clarified water are entrained in the flowing air to produce a gas-laden air stream that is discharged from outlet duct 32 and fed via exhauster 30 into the inlet 29A of scrubber 29 where the gases are neutralized. Exhausted into the atmosphere through outlet 29B of the scrubber is an innocuous and odor-free air stream.

While there has been shown and described a preferred embodiment of an odor control system for wastewater settling tank in accordance with the invention, it will be appreciated that many changes and modifications may be made therein without, however, departing from the essential spirit thereof.

I claim:

1. An odor control system for a settling tank containing a pool of wastewater to be clarified and provided with an elongated effluent trough on one side of which is an upwardly extending weir permitting clarified water at the surface of the pool to spill over into the trough, said system comprising:
   (a) an elongated hood formed by a series of sections mounted over the trough and its weir along the full length thereof and including a side wall that extends downwardly into the pool at a position displaced form the weir to capture noxious gases which are emitted into a region above the clarified water in the trough;
   (b) an inlet duct and an outlet duct coupled to the hood and communicating with said region whereby when the system is in operation air drawn into the region through said inlet duct entrains the emitted gases to produce a gas-laden air stream that flows at a specified velocity through the region and is discharged therefrom through the outlet duct; and
   (c) a closable port formed in each of the series of sections of said hood providing access to said region through said port by test proves to determine while the system is in operation the velocity of the gas-laden stream and the concentration of the gases therein, said said closable ports and said test probes being configured such that said test probes, when inserted in said ports, the effectively seal said ports to prevent the escape of the air stream from the region.

2. A system as set forth in claim 1, further including a scrubber and an exhauster coupled to said outlet duct to exhaust the stream of gas-laden air from the region and to feed it into the scrubber which functions to neutralize said gases before they are discharged into the atmosphere.

3. A system as set forth in claim 2, wherein the velocity of the stream is such as to remove gases from said region at a rate of several changes per hour.

4. A system as set forth in claim 1, wherein said hood is fabricated from fiberglass reinforced plastic material.

5. A system as set forth in claim 1, wherein said ports are closed by a removable cap which when in place is flush with the surface of the hood.

6. A system as set forth in claim 1, wherein said hood is provided with a hatch cover to afford access to said weir.

7. A system as set forth in claim 1, wherein said hood includes a horizontal wall having said ports formed therein and which also functions as a walkway.

8. A settling tank for clarifying wastewater, said tank having an outer wall containing a pool of wastewater so that the water at the surface of the pool is clarified, an outlet in said tank comprising:
   (a) an effluent trough supported at a raised position in the pool against the outer wall of the tank, said trough having a side wall parallel to the tank wall and lying somewhat below the surface of the pool;
   (b) a weir supported on the side wall and extending upwardly therefrom to permit clarified water from the pool to spill over into the trough; and
   (c) a flat walk plate overlying the trough and the weir and including a hatch cover section providing access to the weir, said walk plate extending horizontally from the tank wall to the upper edge of a vertical sidewall that extends downwardly into the pool, said walk plate and said vertical sidewall together acting to confine noxious gases emitted into the region above the trough and the weir to prevent their discharge into the atmosphere, said gases being entrained in air flowing at a specified velocity through said region to produce a specified velocity gas-laden air stream, said walk plate having a closable access port therein in alignment with a vertical center line going through the trough to permit the insertion of test probes to measure the velocity of the stream and the concentration of gases therein while the system is in operation, said said access port and said test probes being configured such that, said test probes when inserted in said port, then effectively seal said port to prevent the escape of the air stream from the region.

* * * * *

UNITED STATES PATENT AND TRADEMARK OFFICE
CERTIFICATE OF CORRECTION

PATENT NO. : 5,176,823
DATED : January 5, 1993
INVENTOR(S) : John J. Roley

It is certified that error appears in the above-identified patent and that said Letters Patent is hereby corrected as shown below:

Column 8, line 24, "proves" should read --probes--

Column 8, line 29, "the" should read --then--

Signed and Sealed this

Twenty-sixth Day of October, 1993

Attest:

BRUCE LEHMAN

Attesting Officer

Commissioner of Patents and Trademarks